(12) United States Patent
Drazek et al.

(10) Patent No.: US 10,870,876 B2
(45) Date of Patent: Dec. 22, 2020

(54) METHOD FOR DETECTING A PRESENCE OR ABSENCE OF AT LEAST ONE FIRST ZONE OF INHIBITION

(71) Applicant: BIOMÉRIEUX, Marcy l'Etoile (FR)

(72) Inventors: Laurent Drazek, Grenoble (FR); Agnés Dupont-Fillard, Les Ardets (FR); Frédéric Pinston, Grenoble (FR); Hervé Rostaing, Le Versoud (FR)

(73) Assignee: BIOMERIEUX, Marcy l'Etoile (FR)

( * ) Notice: Subject to any disclaimer, the term of this patent is extended or adjusted under 35 U.S.C. 154(b) by 0 days.

(21) Appl. No.: 15/743,148

(22) PCT Filed: Jul. 6, 2016

(86) PCT No.: PCT/FR2016/051712
§ 371 (c)(1),
(2) Date: Jan. 9, 2018

(87) PCT Pub. No.: WO2017/006055
PCT Pub. Date: Jan. 12, 2017

(65) Prior Publication Data
US 2018/0208958 A1     Jul. 26, 2018

(30) Foreign Application Priority Data

Jul. 9, 2015 (FR) .................................. 15 56490

(51) Int. Cl.
| | | |
|---|---|---|
| *C12Q 1/04* | (2006.01) | |
| *C12Q 1/18* | (2006.01) | |
| *C12Q 1/20* | (2006.01) | |
| *C12M 1/34* | (2006.01) | |
| *G01N 33/52* | (2006.01) | |

(52) U.S. Cl.
CPC .............. *C12Q 1/04* (2013.01); *C12M 41/36* (2013.01); *C12Q 1/18* (2013.01); *C12Q 1/20* (2013.01); *G01N 33/521* (2013.01)

(58) Field of Classification Search
CPC ... C12Q 1/04; C12Q 1/18; C12Q 1/20; C12M 41/36; G01N 33/521
USPC ........................................................ 435/32
See application file for complete search history.

(56) References Cited

U.S. PATENT DOCUMENTS

| | | |
|---|---|---|
| 5,028,529 A | 7/1991 | Ericcson et al. |
| 2010/0099137 A1 | 4/2010 | Taintor |
| 2013/0029371 A1 | 1/2013 | Belley |

FOREIGN PATENT DOCUMENTS

| | | |
|---|---|---|
| FR | 2988400 A1 | 9/2013 |
| WO | 99/45095 A1 | 9/1999 |
| WO | 00/55357 A1 | 9/2000 |
| WO | 2012/083150 A2 | 6/2012 |
| WO | 2013/160408 A2 | 10/2013 |

OTHER PUBLICATIONS

Jorgensen et al., Antimicrobial Susceptibility Testing: General Principles and Contemporary Practices, Clinical Infectious Diseases, (1998) 26: 973-80.*
European Society of Clinical Microbiology and Infectious Diseases, Determination of minimum inhibitory concentrations (MICs) of antibacterial agents by agar dilution, EUCAST Definitive Document E.Def 3.1, Jun. 2000, 6: pp. 509-515.*
Boedicker et al. "Detecting bacteria and determining their susceptibility to antibiotics by stochastic confinement in nanoliter droplets using plug-based microfluidics." author manuscript published as Lab Chip, vol. 8, No. 8, pp. 1265-1272, 2008.
Baraban et al. "Millifluidic droplet analyser for microbiology." Lab on a Chip, vol. 11, No. 23, pp. 4057-4062, 2011.
Oct. 17, 2016 Search Report issued in International Patent Application No. PCT/FR2016/051712.
Oct. 17, 2016 Written Opinion issued in International Patent Application No. PCT/FR2016/051712.

* cited by examiner

*Primary Examiner* — Jennifer M. H. Tichy
(74) *Attorney, Agent, or Firm* — Oliff PLC

(57) ABSTRACT

A method for detecting a presence or an absence of at least one zone of inhibition, the method including a step consisting in depositing a volume of the sample in liquid form along a deposition zone extending along an axis at the surface of the agar culture medium and a step consisting in depositing a determined amount of a chemical agent at the surface of the agar culture medium, the deposit defining a potential zone of inhibition, the axis of the zone of deposition of the sample intersecting the potential zone of inhibition.

28 Claims, 8 Drawing Sheets

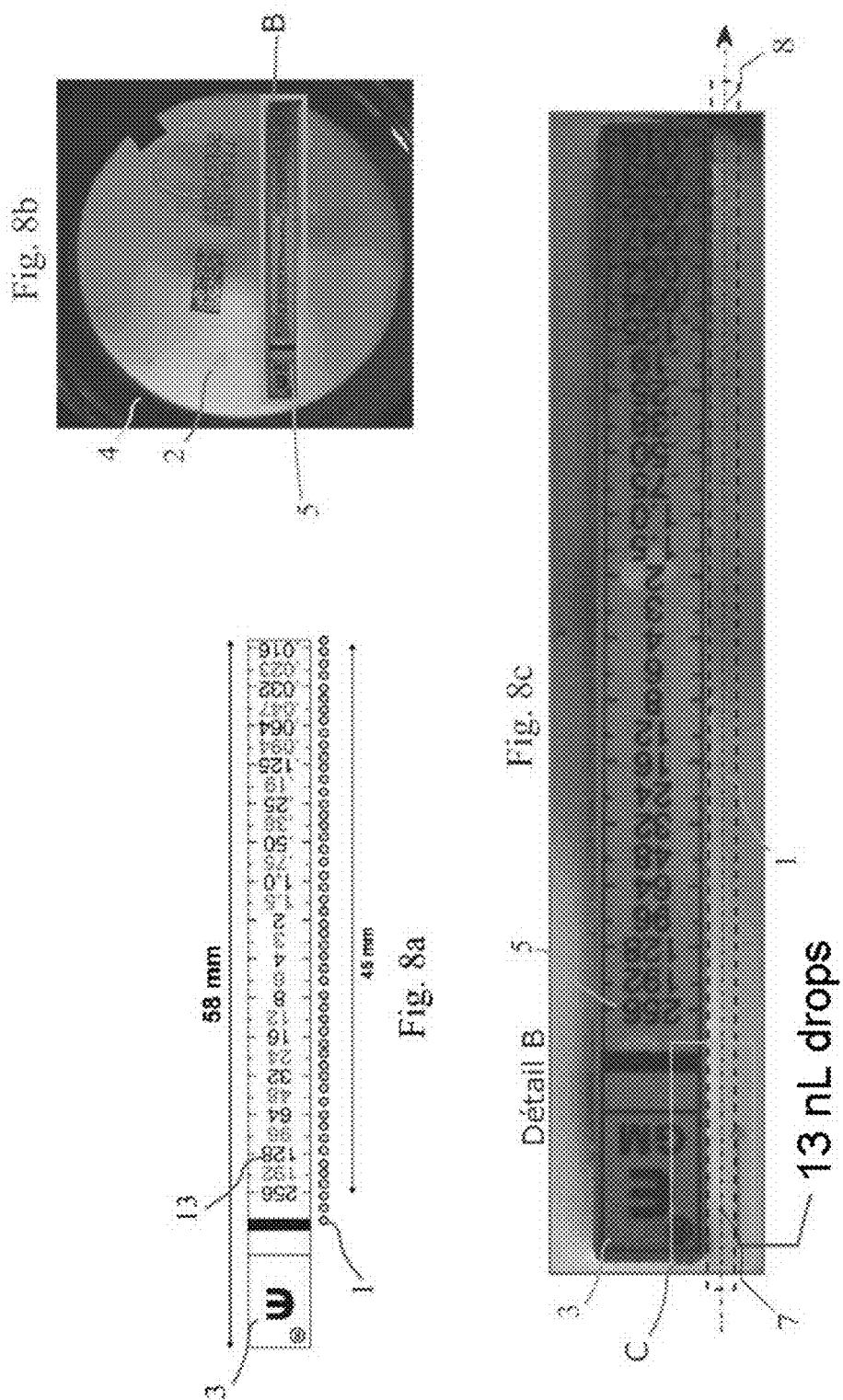

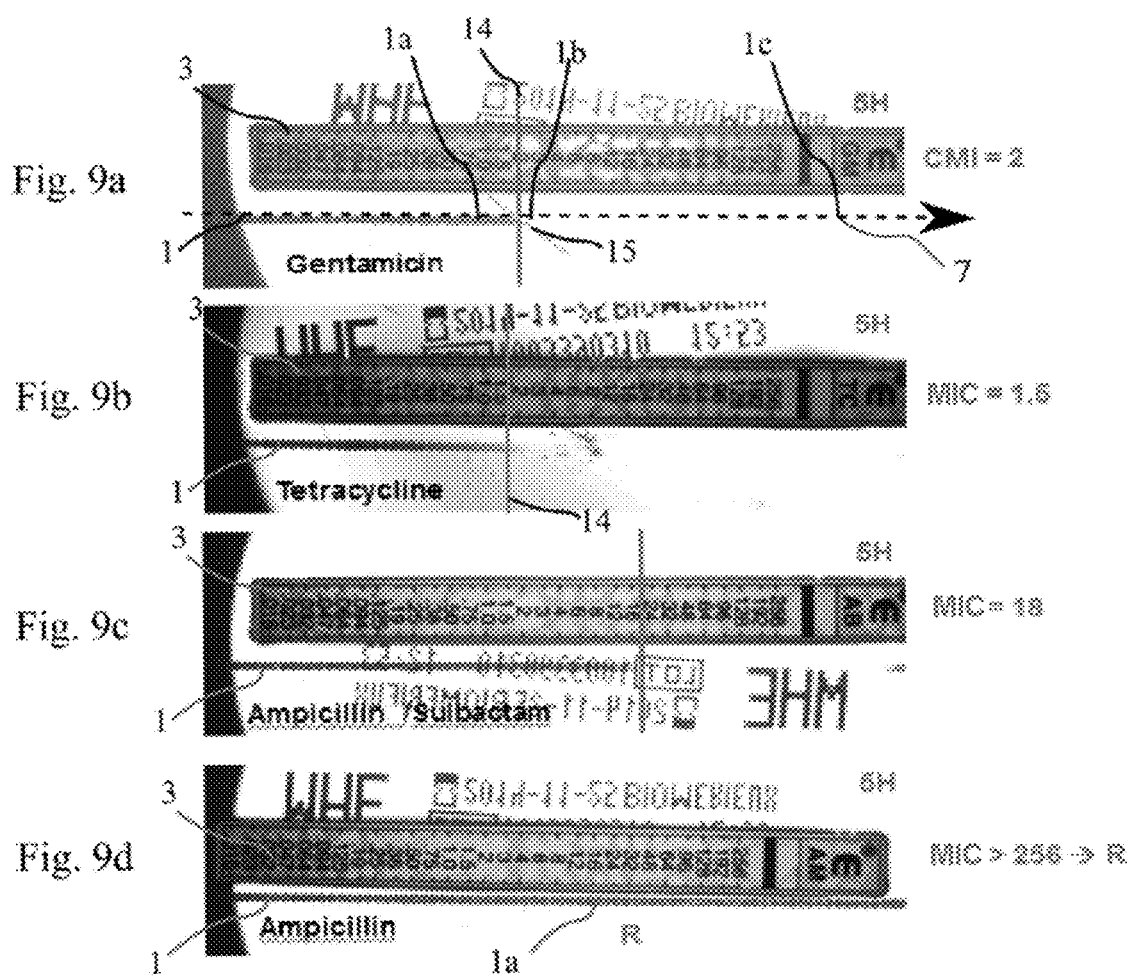

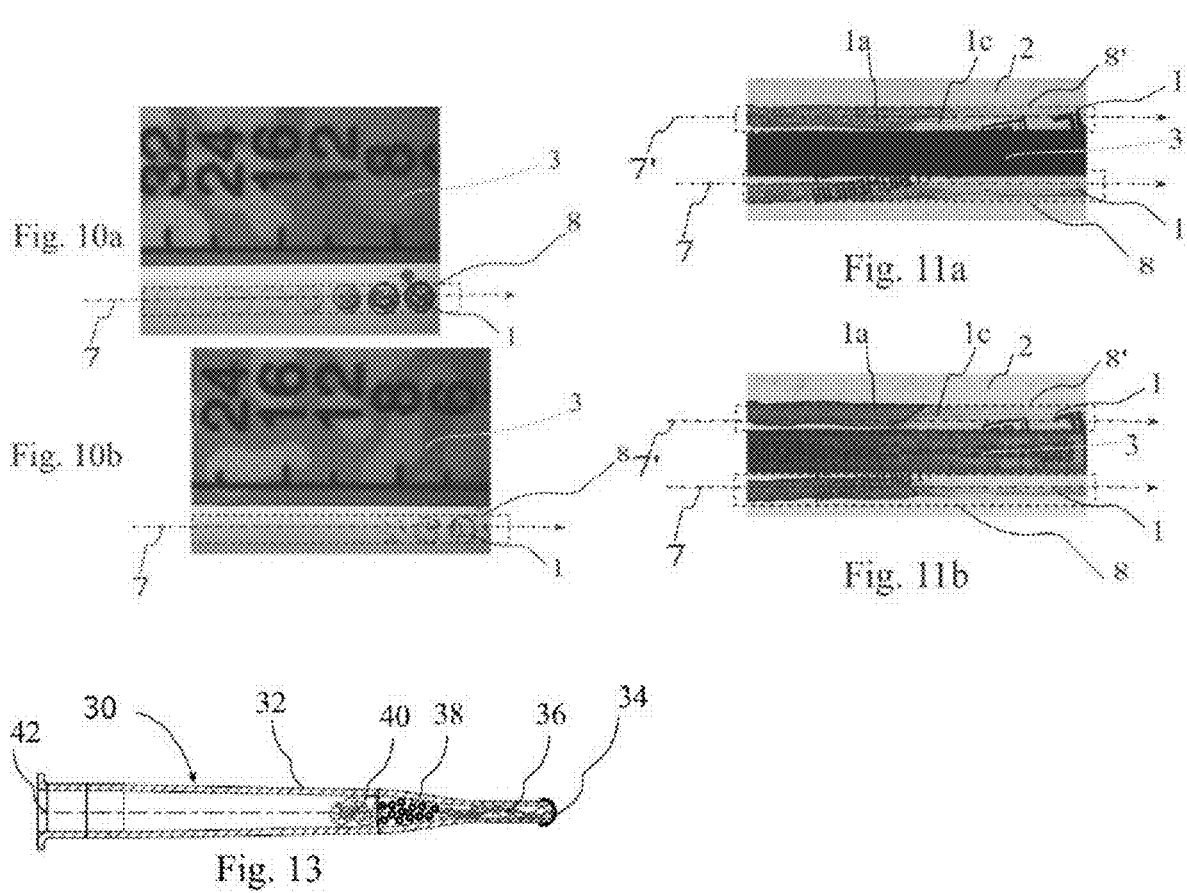

METHOD FOR DETECTING A PRESENCE OR ABSENCE OF AT LEAST ONE FIRST ZONE OF INHIBITION

The technical field of the present invention is that of microbiology. More particularly, the present invention relates to the detection of a presence or an absence of at least one first zone of inhibition of a sample containing or liable to contain microorganisms in the presence of a chemical agent.

More particularly, the present invention relates to tests for determining the sensitivity of a microorganism to an antibiotic.

A conventional test of sensitivity is the disk-diffusion test, often referred to as the Kirby-Bauer method. This standardized method involves the inoculation of an agar culture medium (for example a 90 mm or 150 mm Mueller-Hinton agar) with a sample, generally standardized to 0.5 McFarland, obtained from a microbial isolate. The inoculation may be performed by conventional manual methods, by means of a swab or a loop. Alternatively, the inoculation may be performed by flooding the agar with a suspension standardized to one tenth of 0.5 McFarland, followed by removal of the excess sample. Following the inoculation, one or more paper disks impregnated with defined concentrations of antibiotics are deposited on the surface of the agar. After an incubation period, generally from 16 to 20 hours at 35° C., the diameter of the zone(s) of inhibition around the disks makes it possible to determine the sensitivity of the microorganism present in the inoculated sample to each of the antimicrobial agents impregnated in each disk. Due to the standardization of the Kirby-Bauer method, the results of this method are analyzed by comparing the diameter of each of the zones of inhibition with the recommendations published by regulatory bodies such as NCCLS (National Committee for Clinical Laboratory Standards) or EUCAST (European Committee on Antimicrobial Susceptibility Testing). The results are thus commonly classified according to one of the three following statements: sensitive, intermediate or resistant. These recommendations are therefore reflected in associated reference susceptibility thresholds corresponding to sizes of zones of inhibition for each microorganism in relation to each antibiotic.

"Sensitive" means that growth, or even survival, of the microorganisms present in the sample, in the presence of the antibiotic, is impossible, from a certain concentration of antibiotic. "Intermediate" means that growth of the microorganisms in the presence of the antibiotic is compromised, from a certain concentration of antibiotic. "Resistant" means that growth of the microorganisms in the presence of the antibiotic is possible, at least up to the threshold of toxicity of the antibiotic for the patient to be treated.

Another method for detecting sensitivity to antibiotics uses an antibiotic gradient deposited on an agar medium. For this purpose, paper or plastic strips are impregnated with a concentration gradient of antibiotic. The strips soaked in this way are graduated so as to indicate the antibiotic concentration values present along the strip. One or more strips may be placed on a Mueller-Hinton agar, inoculated beforehand in the same way as the above method. After incubation, an ovoid area of inhibition of microbial growth around each strip appears if the microorganism present in the sample is sensitive to the antibiotic contained in the strip. It is thus possible to deduce a minimum inhibitory concentration (MIC) for microbial growth. The minimum concentration of the antimicrobial agent which makes it possible to inhibit the growth of the microorganism which is generally retained is thus the value of the concentration which can be read on the graduation directly below the point of contact between the zone of inhibition and the long edge of the strip. In other words, the MIC is the concentration visible at the limit of the zone of inhibition, at the boundary between the zone of growth of the microorganisms and the zone of non-growth. More particularly, the MIC can be read by noting the point at which the ovoid area of the zone of inhibition intersects the strip, and by noting the corresponding graduation.

The drawback of these methods is that they are difficult to automate. In particular, the step of inoculation by flooding requires a circular movement and the swirling of the dish by the operator in order to correctly distribute the deposit of the sample over the whole surface of the agar. This particular movement requires a certain technical aptitude by the operator carrying it out, and is particularly difficult to reproduce by a machine. Thus, in order to be carried out in an automated manner, this method requires means for visually checking the deposit in order to ensure that the whole surface of the agar is covered by the sample. Automation of the deposition is also made complex by variations in viscosity between different types of liquid samples which may be used, especially between samples resulting directly from blood culture and resuspended samples. Moreover, the operation for removing excess sample also requires means for precise detection and pipetting of the surface of the agar. Finally, this method requires large volumes of sample, of the order of a milliliter, which increases the biological risk associated with the handling of these samples by the operator.

Automation of the deposition is also long and tiresome with a swab or a loop, especially to cover the whole surface of the culture medium.

Further, automated reading of the zones of inhibition is particularly difficult starting with traditional inoculation methods, whether the disk or the strip method. The zones of inhibition especially have edges with a not very pronounced contrast, which can be difficult to identify by an imaging system.

Finally, another drawback is that these methods require a large volume of sample containing a lot of biomass, especially 1 ml of suspension calibrated to 0.5 McFarland. This amount often requires a prior step of pre-incubation of the sample in the presence of a broth or on an agar medium, in order to be able to harvest the necessary amount of microorganism colonies. This prior step thus delays the time at which a choice of antibiotic treatment suitable for the type of microorganism present may be made by the practitioner. It is thus common for broad-spectrum antibiotics to be administered while waiting for a sensitivity result, this choice sometimes proving ineffective and being known to favor the appearance of resistant microorganisms.

One aim of the present invention is therefore to propose a method for detecting a presence or an absence of at least one first zone of inhibition, making it possible to use a reduced amount of biomass to be inoculated compared to conventional methods and consequently making it possible to reduce the pre-incubation time necessary to produce this biomass. More particularly, it is desirable to be able to reliably and rapidly characterize a response of microorganisms, which are present or liable to be present in the sample, to the presence of the chemical agent. This response is preferentially obtained from culturing for less than 6 hours, resuspended in a small volume of buffer.

A second aim of the present invention is to propose a method which can be readily automated, especially comprising steps of deposition of the sample and of reading of the zones of inhibition which are rapid, reliable and repeatable.

To this end, the present invention relates to a method for detecting a presence or an absence of at least one zone of inhibition, said method comprising the steps consisting in:
a. providing an agar culture medium;
b. providing a sample containing or liable to contain microorganisms in liquid form;
c. depositing a volume of the sample in liquid form along a deposition zone extending along an axis at the surface of the agar culture medium;
d. depositing a determined amount of a chemical agent at the surface of the agar culture medium, said deposit defining a potential zone of inhibition, the axis of the zone of deposition of the sample intersecting the potential zone of inhibition;
e. incubating said agar culture medium;
f. determining the presence or the absence of said first zone of inhibition.

The size of the potential zone of inhibition may be defined as the surface area of the agar, for example if the sensitivity of the microorganism to the chemical agent is unknown and/or if the microorganism is unknown and/or if the presence of a microorganism in the sample is unknown.

In the other case, in which the type of microorganism, for example the genus, species or subspecies, is known, this information makes it possible to obtain information on the presumed sensitivity to the chemical agent from the recommendations of regulatory bodies such as NCCLS (National Committee for Clinical Laboratory Standards) or EUCAST (European Committee on Antimicrobial Susceptibility Testing). These recommendations present, for each pair formed of a chemical agent and of a given microorganism, the size of the potential zone of inhibition after incubation for a given time, depending on whether the microorganism is sensitive, intermediate or resistant to the chemical agent.

Thus, according to an advantageous detection method according to the invention, the sample contains a culture of microorganisms of known type, the area of the potential zone of inhibition then being defined by said type of microorganisms.

The steps of deposition of the sample may especially be automated by means of a robotic arm or a pipetting robot, having a tool holder which moves translationally according to three degrees of freedom, such as a Hamilton® Microlab Star pipetter. The steps for determining the presence of the zones of inhibition may especially be carried out by means of a detection device comprising a light source and a capturing means so as to capture an image of the sample deposited on the culture medium, then by carrying out a visual examination or an automated processing of the image obtained in this way.

The advantage of the invention is therefore to be able to propose a method which can be readily automated, especially since the step of depositing a volume of the sample in liquid form is carried out according to a deposition zone extending along an axis at the surface of the agar culture medium. It is thus easy for a programmable automated device to carry out this deposition step along an axis, the coordinates of which are pre-programed or are determined by conventional imaging methods. Further, reading the result of the detection method is also greatly facilitated due to the fact that the sample, and therefore the zone of inhibition, are located in a more restricted zone in the culture medium than in a conventional method of flooding or loop inoculation. The axis of deposition of the sample will thus be rectilinear, or even generally rectilinear. Variations of the axis of deposition, using consecutive portions of straight lines, portions of curves or curves, may be envisaged if the sample is deposited in immediate proximity to the zone of deposition of the chemical agent. Especially in the case of a support having a concentration gradient of chemical agent, such as a strip, it may be important to deposit the sample along a generally rectilinear axis, preferentially adjacent to the support of the chemical agent, regardless of the shape of the support.

According to one embodiment:
the volume of the sample is deposited by means of a predefined deposition technique which is suitable, for a given biomass of microorganisms in a volume of sample in liquid form, for depositing said volume over a maximum surface area of the agar culture medium so as to obtain a substantially homogeneous surface density of microorganisms which is greater than a predefined threshold.
the sample is obtained by means of pre-culture of a crude sample, the pre-culture comprising a phase of isolation of a strain of microorganism followed by a phase of incubation of said strain so as to increase the biomass of microorganisms, said biomass depending on the duration of incubation; and
the duration of incubation of the crude sample is chosen to be less than 10 hours, advantageously less than 6 hours, and even more advantageously between 3 hours and 6 hours, the surface area of deposition of the volume of sample by means of the predefined deposition technique being chosen to obtain said density.

In other words, it is sought to deposit a liquid layer of the sample which has a concentration which is both minimal in terms of microorganisms and substantially homogeneous. In the opposite case, a zone not having these concentration characteristics could present very poor growth of the microorganisms, which would distort the measurement since such a zone would be identified as a zone of inhibition. Yet, for a given deposition technique, for example by flooding, by means of a swab or a loop, a minimal biomass is necessary per unit of surface area. In the prior art, inoculation consists in depositing over the whole of the surface of a Petri dish, which requires a large biomass, and consequently a long incubation time to obtain this biomass. According to the invention, a smaller deposition zone is targeted, the necessary biomass thus also being reduced, and therefore the incubation time to obtain this biomass being reduced. The inventors have thus observed that an incubation time of less than 6 hours makes it possible to obtain the sufficient biomass to make a measurement of MIC.

In particular, the duration of incubation necessary to obtain sufficient biomass for a deposition over the whole of the surface of the agar culture medium at said density is greater than 20 hours, which corresponds to the diameter of a Petri dish 9 cm in diameter, inoculated over the whole surface thereof.

According to a first embodiment, the step c) of the detection method according to the invention consists in:
c. depositing a volume of the sample in liquid form in a continuous line along a deposition zone extending along an axis at the surface of the agar culture medium.

The volume of sample deposited in the form of a continuous line may have a concentration of between 0.0005 McFarland and 0.5 McFarland. The invention may therefore be applicable to sample concentrations that are conventional: between 0.5 McFarland and 0.1 McFarland, weak: between 0.1 McFarland and 0.01 McFarland, or even very weak: between 0.01 McFarland and 0.0005 McFarland, these concentrations being able to be produced with a minimal incubation time or even without incubation.

According to a second embodiment, the step c) of the detection method according to the invention consists in:
c. depositing a volume of the sample in liquid form in droplets along a deposition zone extending along an axis at the surface of the culture medium.

The sample may thus be deposited in discrete form if the droplets are spaced apart by a distance greater than their diameter once deposited. Advantageously, the deposited droplets are spaced apart by a predetermined interval, preferentially predetermined by the area of the potential zone of inhibition and/or the diameter of the deposited droplets. For example, the centers of the deposited droplets may be spaced apart by an interval in the millimeter range, preferentially by a millimeter, in order to be able to rapidly compare the number of inhibited droplets with the recommendations of the regulatory bodies. Indeed, these recommendations describe, for a given microorganism and chemical agent, the size in millimeters of the zone of inhibition, measured depending on whether the microorganism is sensitive, intermediate or resistant. By counting the number of inhibited drops and/or the number of drops exhibiting growth, a sensitivity result may be readily obtained. Thus, in an alternative embodiment of the method, the latter comprises a step consisting in determining the number of inhibited droplets in the potential zone of inhibition and/or the number of non-inhibited droplets in the zone of deposition of the sample, in order to detect the presence of a potential zone of inhibition and to deduce therefrom the sensitivity of the microorganism present in the sample to the chemical agent.

The volume of each deposited droplet is advantageously between 1 nl and 10 µl. The method is therefore applicable to samples of low to very low volumes, especially samples originating from pediatric hospital services. Another advantage of the method is that it does not consume too much of the volume of the sample, which makes it possible to carry out other analyses from the same sample.

Thus, the inventors have estimated that an advantageous embodiment of the method according to the invention could be implemented starting from an amount of microorganisms contained in each deposited drop of between 1 microorganism per drop and $10^6$ microorganisms per drop, preferentially of $10^4$ microorganisms per drop. These orders of concentration therefore make it possible to analyze samples without incubation or with a limited duration of incubation making it possible to reach the necessary concentration.

The deposition of the chemical agent is for example reduced to a droplet of water containing the chemical agent. The detection method according to the invention is thus directly applicable to tests using supports impregnated with chemical agent. Thus, the step d) may advantageously consist in:
d. depositing a support impregnated with a determined amount of a chemical agent at the surface of the agar culture medium, said support defining a potential zone of inhibition, the zone of deposition of the sample intersecting the potential zone of inhibition.

The deposition of the chemical agent is for example carried out on an impregnated paper or plastic support. This support may for example be a disk impregnated with the chemical agent, the disk being shaped overall as a thin cylindrical portion. The disk comprises an amount of chemical agent which is generally homogeneous in its volume.

The impregnated support may thus be a disk containing a determined amount of chemical agent. In the case of a disk, the detection method according to the invention may comprise an additional step consisting in measuring the distance between the center of the disk and the first zone of inhibition in order to estimate the sensitivity of the microorganisms contained in the sample to the chemical agent. Advantageously, the axis of deposition of the sample intersects the center of the disk deposited on the medium. Preferentially, the method may be continued with a step consisting in classifying the microorganism according to a criteria-based classification, for example: Sensitive, Intermediate or Resistant, from a sensitivity chart corresponding to the microorganism present in the sample and to the chemical agent. This chart may especially be obtained experimentally by learning or from recommendations from regulatory bodies.

According to a particular embodiment of the invention, the step d) consists in:
d) carrying out at least two depositions of a determined amount of a chemical agent at the surface of the agar culture medium, said deposits each defining a potential zone of inhibition, the axis of the zone of deposition of the sample intersecting all the potential zones of inhibition.

This particular mode makes it possible especially to study the effects of synergy between several chemical agents, especially impregnated on disks. For example, two disks comprising two different agents may be deposited on a culture medium, the axis of deposition of the sample intersecting the center of these two disks. In another example, four disks comprising four different agents are deposited on a culture medium, the axis of deposition of the sample intersecting the center of these four disks such that it follows the edges of a rectangle.

The impregnated support is for example a thin strip of an overall rectangular conformation. The strip comprises for example a concentration of chemical agent which follows an increasing concentration gradient from one short edge to the other opposite short edge of the strip. Thus, in an alternative embodiment of the detection method according to the invention, the impregnated support is a strip containing a concentration gradient of chemical agent, the volume of the sample in liquid form being deposited parallel and preferentially adjacent to at least one long edge of said strip. Adjacent means that the deposition is carried out as close as possible to the long edge of the strip, without however the deposited liquid sample being in contact with the strip. Indeed, it is not very desirable for the sample to be in direct contact with the strip, since this may wet the strip and thus locally modify the diffusion of the chemical agent into and onto the agar.

Advantageously, the method comprises an additional step consisting in:
locating a boundary between the first zone of inhibition and the zone of growth of the microorganisms;
determining a minimum inhibitory concentration of the chemical agent from the location of said boundary.

The step of locating a boundary between the first zone of inhibition and the zone of growth of the microorganisms may be carried out visually or by capturing an image of the culture medium following the step of incubation using an acquisition means, then by looking for a straight line or an arc present at the intersection between the zone of growth and the zone of inhibition of the sample. According to techniques known to those skilled in the art, the boundary between the zone of inhibition and the zone of growth may be obtained from an image or from a combination of images. This or these images advantageously make it possible to visualize both the graduations present on the strip and the boundary between the zone of inhibition and the zone of growth. A conventional technique consists in obtaining a plan view image of the graduations of the strip and in combining it with a transmission image of the culture medium.

A conventional method consists, starting from a digital image, in defining a Cartesian reference frame, the abscissa axis of which is typically defined as the main axis of the strip. It is then possible to locate a defined mark on the strip, typically known text such as a graduation. For example, the characters "256", corresponding to the concentration at 256 µg·ml$^{-1}$ of chemical agent, may be located in the reference frame. The defined mark is able to consist of virtually any other indication. The defined mark may also correspond to one of the short edges of the strip. The defined mark then comprises Cartesian coordinates in the Cartesian reference frame. Similarly, the long edges of the strip may be readily recognized by conventional image processing means in order to obtain their coordinates in the reference frame.

Subsequently, the image is processed in order to find the boundary between the zone of inhibition and the zone of growth. This step may optionally comprise a smoothing operation to homogenize the image. Such a smoothing operation is for example carried out using Gaussian filtering. The smoothing operation is preferably carried out several times, especially seven times. This step may optionally comprise an operation of stretching the dynamics of the pixel intensity of the image to form a contrast histogram of the image, the contrast to be considered being between dark pixels and light pixels of the image. This results in determination of the useful dynamics of the image. This step may thus comprise an operation of thresholding of the image, which comprises for example detection of a threshold and determination of a contour from a digitization of the image. From this contour, a straight line or an arc may then be extrapolated, which represents the boundary between the zone of growth and the zone of inhibition, this straight line or this are being searched for in a zone of pixels close to the long edge of the strip, for example at less than one centimeter from the long edge.

From this boundary, an operation for estimating a minimum inhibitory concentration may be carried out. A possible method consists in determining the abscissa coordinates of the intersection between the straight line or the arc obtained and the long edge of the strip. Alternatively, a method may consist in determining the abscissa coordinates of the intersection between the straight line or the arc obtained and the abscissa axis of the Cartesian reference frame. Once the abscissa is obtained, in relation with the origin of the reference frame and the known length of the strip, the minimum inhibitory concentration may be determined. In certain cases, it is possible that the culture medium only contains totally inhibited or totally growing droplets, that is to say in which there is no frontier between a zone of growth and a zone of inhibition which is visible or which can be determined. In this case, the MIC value may be directly obtained by counting the droplets in relation with the deposition interval, or from the location of the droplets in the reference frame, especially the location of the first non-inhibited droplet along the increasing concentration gradient of chemical agent. Alternatively the MIC value may be directly obtained from the location of the last inhibited droplet along the increasing concentration gradient of chemical agent.

Culture medium means an agar medium, having an agar layer or similar. Culture media are commonly found in a Petri dish or in dehydrated form applied to a support, generally a film. Nonlimitingly, other types of culture media may be used, such as culture media on fibrous support or else media on paper support.

The chemical agent is especially an antibiotic, an antifungal agent, an antimycobacterial, or a similar compound.

Liable to contain means that the presence of microorganisms in the sample may be suspected from the type of sample taken or else the symptoms of the patient or of the animal from which the sample is taken. However, the type of microorganism liable to be contained in the sample is then unknown. In the case of searching for mastitis in cows, for example, it may be more effective to directly determine a minimum inhibitory concentration by conventional chemical agents before knowing the identification of the type of microorganism present in the sample taken directly from the cow's udder. An effective treatment of the infection with the microorganism may then be prescribed.

Other features and advantages of the present invention will become apparent on reading the description which will be given of exemplary embodiments, referring to the figures in the appended drawings, in which:

FIG. 8a illustrates a schematic view of a second example of implementation of the invention.

FIGS. 8b, 8c and 8d illustrate the second example of implementation of the invention.

FIGS. 9a to 9d illustrate the second example of implementation of the invention for four different antibiotics.

FIGS. 10a and 10b illustrate a portion of the strips and the droplets close to said strips after 5 hours of incubation of a sample of *Escherichia coli* ATCC 35218 at 0.5 McFarland and 0.01 McFarland in the presence of ampicillin/sulbactam.

FIGS. 11a and 11b illustrate a third method of implementation of the invention.

Figure 12:
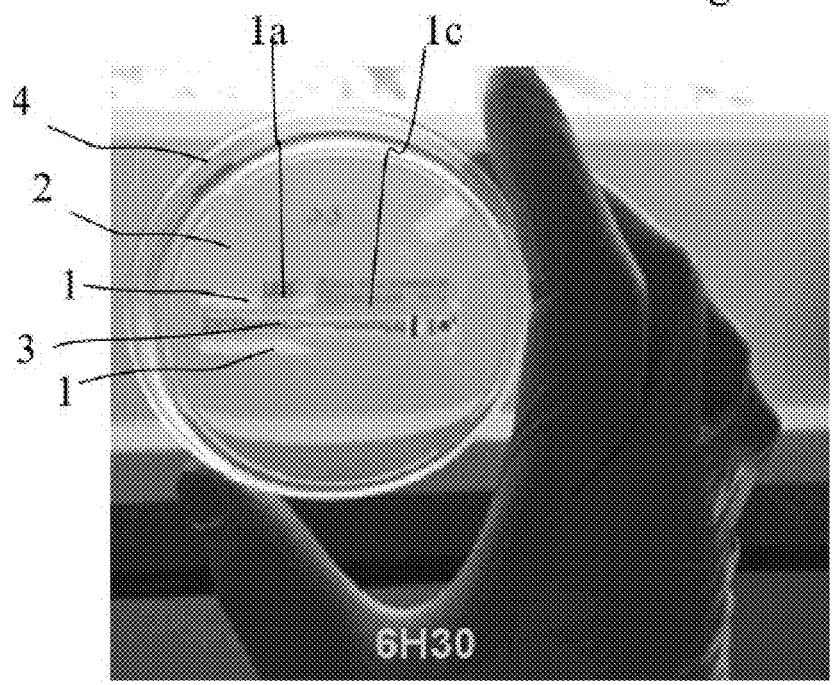

FIG. 12 illustrates a visual examination after 6 h 30 of incubation of the inoculated medium according to the third method of implementation of the invention.

FIG. 13 illustrates an example of a sampling tool which may be used according to the third method of implementation of the invention.

Figure 1:
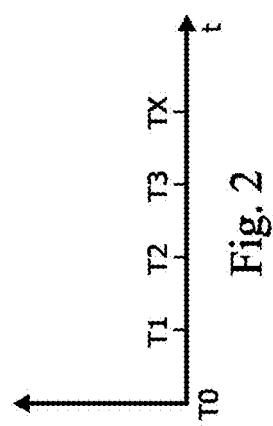
FIG. 1 is a sectional view of a Petri dish used to implement a detection method of the present invention.
Figure 3:
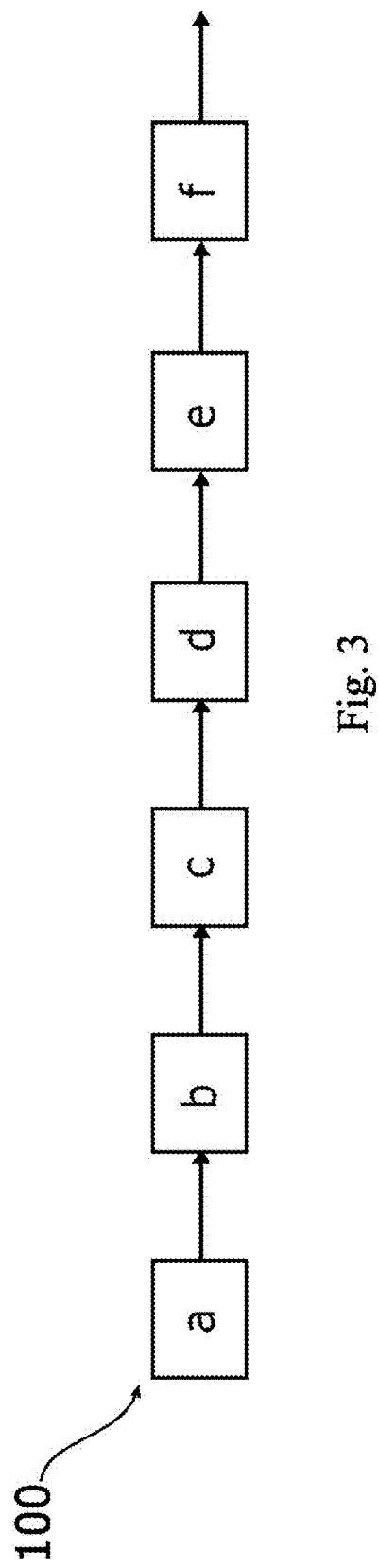
FIG. 3 is a schematic illustration of sequences of the detection method of the present invention.

With reference to FIGS. 1 and 3, in the medical and/or pharmaceutical field, it is common to have to use a method 100 for the detection of a presence or an absence of a zone of inhibition on a culture medium 2 of a sample 1 in the presence of a chemical agent 5 soaked onto a support 3. The culture medium 2 is contained in a Petri dish 4, for example a Petri dish with a diameter greater than or equal to 9 cm, and receives the sample 1 containing or liable to contain microorganisms, and also the chemical agent 5 which is able to inhibit growth of certain microorganisms. The microorganisms are chosen, without preference, from bacteria, yeasts or fungi. Alternatively, the method according to the present invention may be applied to plant or animal cells. The culture medium 2 is preferentially an agar, a layer of agar or similar. The culture medium 2 may also be a dehydrated culture medium on paper support or fibrous support. The medium is then rehydrated by the sample. The chemical agent 5 is especially an antibiotic, an antifungal agent, an antimycobacterial, or a similar compound.

More particularly, it is desirable to be able to reliably and rapidly characterize a response of the sample containing or liable to contain the microorganisms 1 to the presence of the chemical agent 5, such a response being commonly classified according to one of the following three statements: sensitive, intermediate or resistant. It may also be desirable to obtain a value of minimum inhibitory concentration of chemical agent able to inhibit the growth of microorganisms present in the sample.

Figure 2:
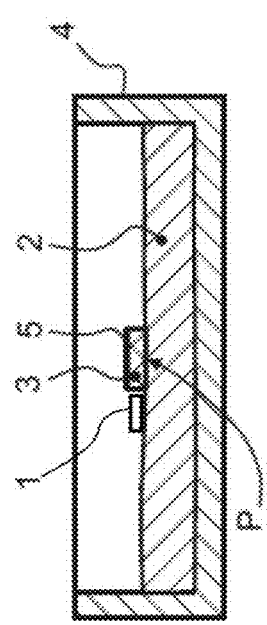
FIG. 2 is a schematic view of the detection method of the present invention.

Such a detection method 100 especially is frequently applied in the field of medical, pharmaceutical and/or veterinary diagnostics, used for the detection of a disease in a patient or an animal. As a result, such a detection method 100 is desired to be reliable in the sense that the nature of the abovementioned response of the microorganisms contained, or liable to be contained, in the sample 1 to the chemical agent 5 is wished to be certain, without doubt or ambiguity. Also as a result, such a detection method 100, the successive sequences of which are illustrated in FIGS. 2 and 3, is desired to be rapid with a response time, which runs between an initial time T0 at which the sample is placed in contact with the chemical agent 5, and a detection time TX at which said reliable response is obtained, which is desired to be as short as possible, and is especially less than eight hours. Also as a result, it is desirable for such a detection method 100 to comprise appropriate repeatability. Such aims are advantageously achieved from the implementation of the detection method 100 of the present invention.

In general terms and with reference to FIG. 3, the detection method 100 of the present invention comprises a step a) of providing an agar culture medium 2, and a step b) of providing a sample 1 containing or liable to contain microorganisms in liquid form, for example a crude sample taken directly from the patient. In this case, the crude sample may undergo a pre-culture phase making it possible to isolate strains of microorganisms present, for example in the case of a sample comprising a diverse range of microorganisms, and an incubation of the selected and isolated microorganisms. The sample 1 is also for example a prepared sample, especially filtered, centrifuged and/or purified in a similar manner. The sample 1 may have a biomass of microorganisms which is sufficient to be validly analyzed, such as a standard of a concentration of between 0.0005 McFarland and 0.5 McFarland. The sample 1 is for example urine, blood, cerebrospinal fluid or a similar biological fluid.

A volume of the sample in liquid form is then deposited in step c) along a deposition zone extending along an axis at the surface of the agar culture medium. The sample may be deposited in droplets, especially by means of a manual pipette or an automated pipette. The droplets may advantageously have an identical volume and be spaced apart by a predetermined interval P, P being the distance between the centers of two consecutive droplets. In the case in which the diameter of the droplets, once deposited, is greater than the value of the interval P, the droplets then form a liquid deposit in a continuous line.

The sample may also be deposited by a swab, especially a flocked or fibrous swab dipped in a volume of the sample then moved along an axis on contact with the agar medium. Alternatively, a pipetting device comprising filtration means, as described in the international application published under the number WO2012/083150 A2, may be used to pipette and filter a volume of sample and to deposit it by smearing on contact with the surface of the agar culture medium. The movement of the swab or of the pipetting device comprising filtration means described above on contact with the agar thus makes it possible to form a deposit of the sample in a continuous line, this line extending along an axis.

The method is continued in the step d) by depositing a determined amount of a chemical agent at the surface of the agar culture medium, said deposit defining a potential zone of inhibition, the axis of the zone of deposition of the sample intersecting the potential zone of inhibition. Alternatively, this deposition may be carried out before the sample is deposited. The initial time T0 is considered to be the moment at which the sample and the chemical agent are brought into contact at the surface of the culture medium.

The method is continued in the step e) by incubating the agar culture medium.

The method is continued in the step f) which consists in determining, at an incubation time TX, the presence or the absence of said first zone of inhibition of the sample around the zone of deposition of the chemical agent, in the potential zone of inhibition.

A first example of implementation of the invention will be detailed according to FIGS. 4a to 4f which illustrate Petri dishes 4 (for example Petri dishes with a diameter of greater than or equal to 9 cm) in plan view.

Figure 4A:
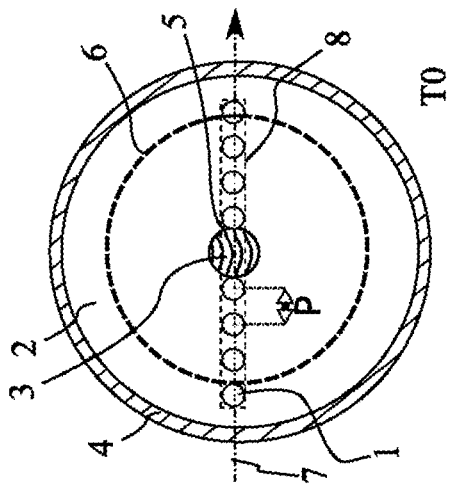
FIGS. 4a to 4f illustrate a first embodiment of the detection method according to the present invention.

With reference to FIG. 4a, the first example of implementation of the detection method according to the present invention comprises a step of providing an agar culture medium 2 in a Petri dish 4.

A disk 3 impregnated with a determined amount of a chemical agent 5 is deposited at the surface of the agar culture medium, said deposit defining a circular potential zone of inhibition 6 around the disk.

Figure 4D:
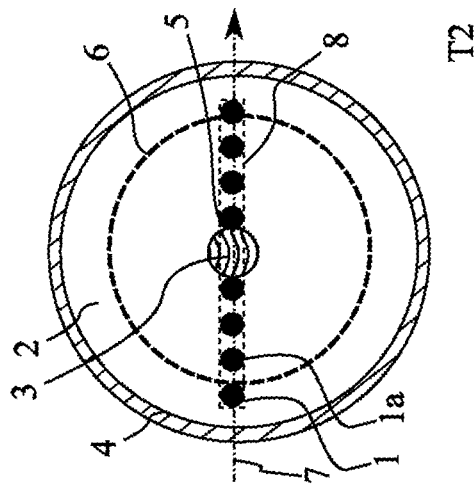
Figure 4B:
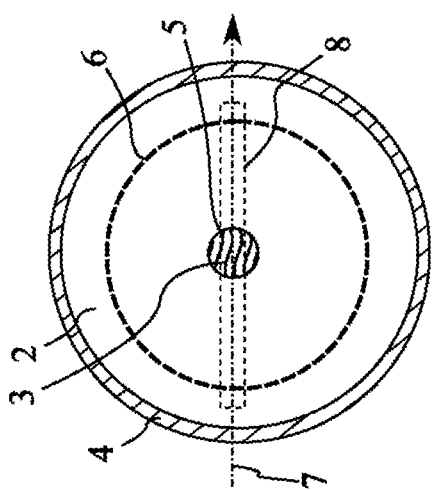

According to FIG. 4b, an axis of deposition 7 intersecting the potential zone of inhibition 6 and the center of the disk 3 is defined. This axis also defines a zone of deposition 8 of the sample 1 which is generally rectangular and equally distributed on either side of the axis of deposition.

Figure 4E:
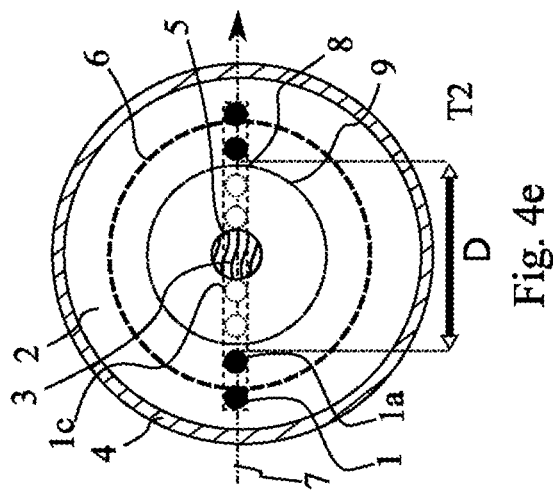
Figure 4C:
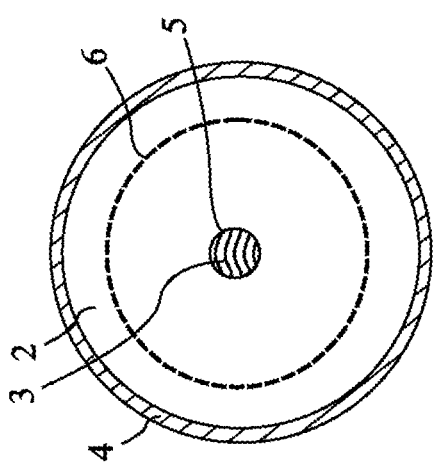

According to FIG. 4c, a liquid sample 1 is deposited at T0 in the form of multiple droplets at the surface of the culture medium 2 in the zone of deposition 8 and along the axis 7. The droplets are spaced apart by an interval P, corresponding to the distance between the center of two consecutive droplets. The incubation of the culture medium then begins.

According to FIG. 4d, at the time T1 after an incubation time, the presence of a first zone of inhibition 9 of the sample 1 is determined, for example by visual analysis. Indeed, some droplets exhibit bacterial growth 1a, while others do not exhibit any bacterial growth, 1c. At the intersection between the first zone of inhibition 9 and the zone of deposition 8 of the sample, certain droplets exhibit a growing portion and an inhibited portion 1b. It is thus possible at this time to demonstrate the presence of microorganisms in the sample and also the inhibition of the growth of these microorganisms in the presence of the chemical agent 5. The zone of inhibition 9 has a diameter D which may especially be measured with a caliper.

According to FIG. 4e, at the time T2 after a longer incubation time, the surface of the first zone of inhibition 9 and the diameter D thereof are stable and no longer vary. It is thus possible at this time to reliably measure the size of the zone of inhibition. This determination is particularly easy in the case of FIG. 4e, in which certain droplets exhibit bacterial growth 1a while others do not exhibit any bacterial growth 1c, a simple counting operation in relation with the deposition interval P between each drop therefore making it possible to determine the sensitivity of the microorganism to the chemical agent. Further, by obtaining an identification of the microorganism present and by comparing the size of the zone of inhibition with the recommendations of regulatory bodies for the pair of chemical agent 5-microorganism present, it is also possible to classify the strain as "sensitive", "intermediate" or "resistant".

Figure 4F:
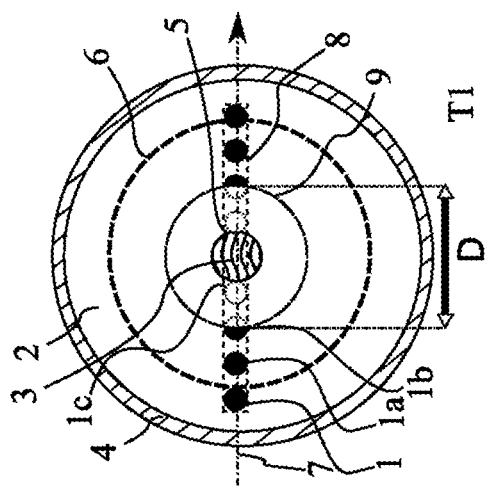

According to FIG. 4f, it is probable that, at a time T2, the first zone of inhibition 9 is no longer visible or is greatly reduced and that some, or even all, of the droplets exhibit bacterial growth 1a. It is thus possible at this time to determine that the type of microorganism present in the sample 1 is resistant to the chemical agent 5. It is also possible that no zone of inhibition is apparent, regardless of the duration of incubation, demonstrating the resistance of the microorganism to the chemical agent.

In order to implement a method according to the invention, for example a capture device comprising a capture means and a light source so as to capture an image of the sample deposited on the culture medium in the presence of a chemical agent.

Figure 5:
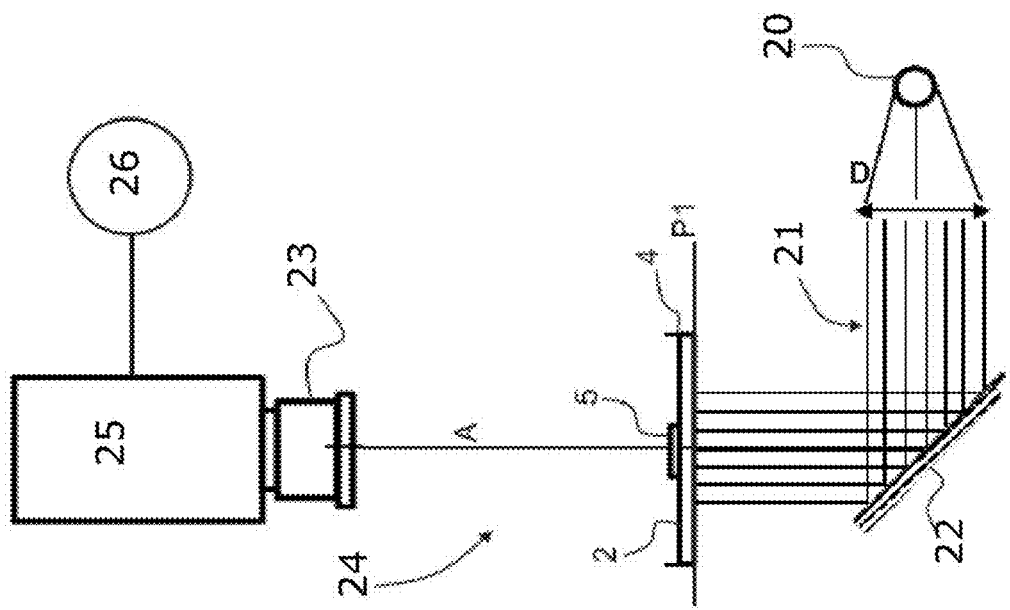
FIG. 5 is a schematic illustration of a device for capturing images by shadowgraphy.

An example of a shadowgraphy capture device 24 is illustrated in FIG. 5. This device comprises a capture means 25. The capture means 25 comprises a capture axis A which is preferentially arranged orthogonally relative to a first plane P1 along which the culture medium 2 extends. The capture means 25 is advantageously directly over the Petri dish 4 so as to take a plan view of the culture medium 2. The capture means is for example a CCD camera, especially of Basler piA2400—17 gm type, which is fitted with a telecentric lens 23. The light source 20 is preferentially a collimated illuminator able to produce light rays 21 parallel to one another which reach the culture medium 2 orthogonally after having been reflected by a mirror 22. The light source 20 may comprise a plurality of diodes comprising a range of emission equally in the red, green, blue and white. The light source 20 is for example of the Opto Engineering—LTCL 048-W type. The telecentric lens 23 is especially of the Opto Engineering—TC23 048 type, comprising a focal field of 46×38.5 mm and a working distance of 134.6 mm. Advantageously, the device 24 may comprise calculating means 26, comprising for example image processing and analysis means, the calculating means 26 constituting a processor which the capture device 24 comprises. Advantageously, the device 24 may comprise one or other light source(s) (not shown) arranged above the culture medium and directed towards the culture medium. These sources make it possible for example to optimally illuminate the printed portion of the support impregnated with chemical agent, especially so as to more readily locate a defined mark on the support such as one or more character(s) printed on the support.

Figure 6A:
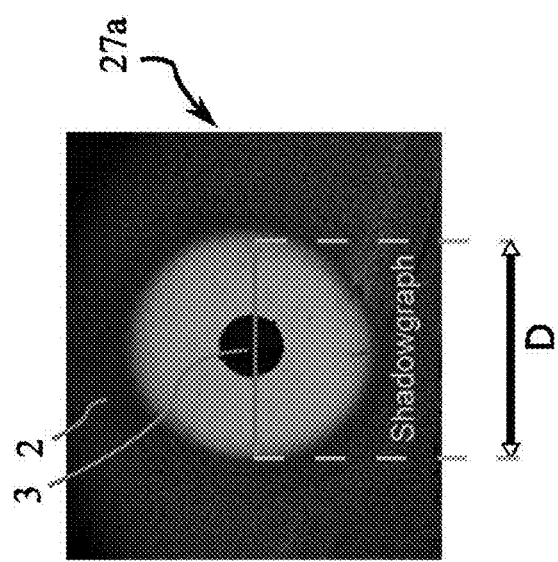
FIGS. 6a and 6b illustrate plan-view images of a Petri dish used for carrying out an embodiment of the detection method according to the present invention in comparison with a conventional technique.
Figure 6B:
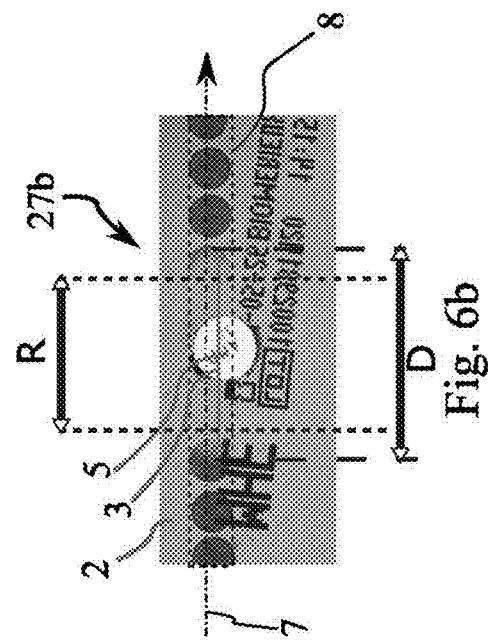

FIGS. 6a and 6b make it possible to compare the results of a traditional method for detecting a presence or an absence of at least one first zone of inhibition with the method according to the invention. In order to perform this comparison, two Mueller Hinton E agars (bioMérieux Ref. 413822) are inoculated with an inoculum originating from a culture of *Staphylococcus aureus* ATCC 25923 (American Type Culture Collection) at a concentration of 0.5 McFarland. The first agar is inoculated by flooding with a volume of approximately 1 ml, while 10 3 µl droplets, separated by an interval of 5 mm, are deposited at the surface of the second agar along an axis 7 in a zone of deposition 8. A soaked disk 3 containing 10 pig of ampicillin is also deposited on each of the agars. In FIG. 6b, the disk is deposited so as to intersect the axis 7 of deposition of the droplets and the zone 8 of deposition of the sample. The two agars are then incubated at 37° C. for 6 hours 30 minutes. Following this incubation time, a plan-view image of each agar is captured by means of a shadowgraphy capture device 24 as described previously, making it possible to obtain the images 27a and 27b of the FIGS. 6a and 6b. At the time of capturing the images 27a and 27b, it is thus possible to observe a diameter D corresponding to a zone of inhibition, similar across the methods and greater than the reference threshold R defined by EUCAST. Indeed, the diameter D of the zone of inhibition is 22 mm, the reference threshold R between sensitive and resistant defined by EUCAST being equal to 18 mm. The method according to the invention therefore makes it possible to use a minimal volume of sample while obtaining an identical result of sensitivity to a chemical agent. Numerous techniques known to those skilled in the art may be employed in order to determine the diameter D in an automated manner. For example, one method may consist in identifying the axis of deposition of the drops and also the center of the disk from a digital image of the culture medium. It is subsequently possible to extract an intensity profile of the pixels of the image along an axis passing through the center of the disk and along, or parallel to, the axis of deposition of the droplets. From this intensity profile, the greatest contrast transitions on either side of the disk are sought. These transitions may be sought by seeking the position in the profile of the first rising edge, or the maximum value of the first derivative of the profile. The two positions obtained on either side of the disk then correspond to the diameter D of the zone of inhibition sought.

A second example of implementation of the invention will be detailed according to FIGS. 7a to 7f.

Figure 7A:
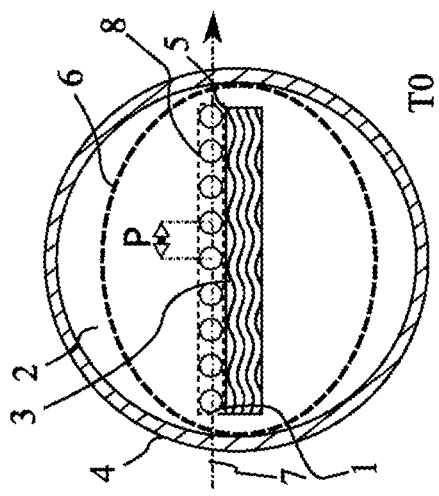
FIGS. 7a to 7f illustrate a second embodiment of the detection method according to the present invention.

With reference to FIG. 7a, the second example of implementation of the detection method according to the present invention comprises a step of providing an agar culture medium 2 in a Petri dish 4, for example a Petri dish with a diameter greater than or equal to 9 cm.

A strip 3 impregnated with a determined amount of a chemical agent 5 is deposited at the surface of the agar culture medium, said deposit defining an ovoid potential zone of inhibition 6 around the strip.

Figure 7D:
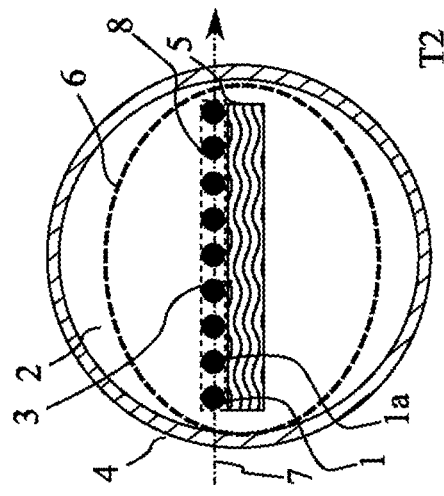
Figure 7B:
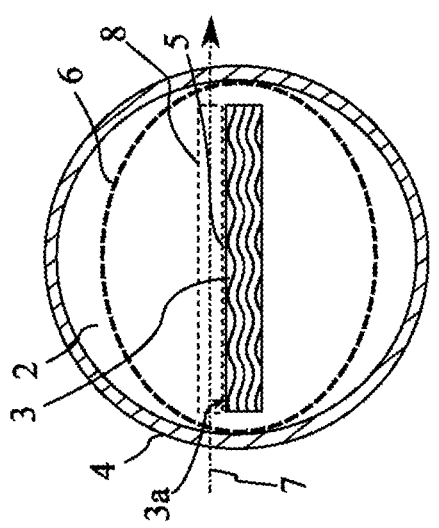

According to FIG. 7b, an axis 7 of deposition intersecting the potential zone of inhibition 6 and parallel to one of the long edges 3a of the strip 3 is defined. This axis also defines a zone of deposition 8 of the sample which is generally rectangular and equally distributed on either side of the axis of deposition.

Figure 7E:
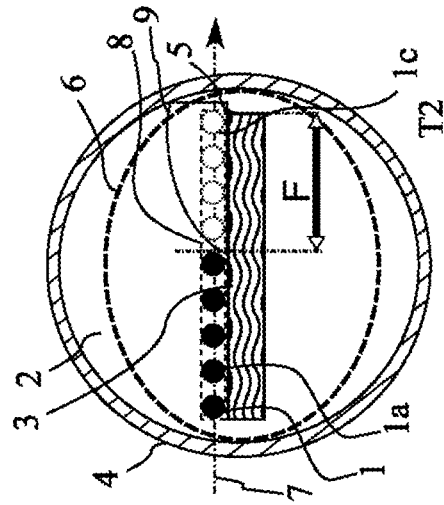
Figure 7C:
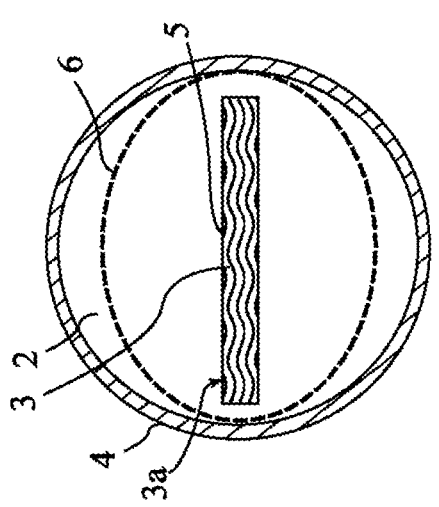

According to FIG. 7c, a liquid sample 1 is deposited at T0 in the form of multiple droplets at the surface of the culture medium 2 in the zone of deposition and along the axis 7. The droplets are spaced apart by an interval P, corresponding to the distance between the center of two consecutive droplets. The incubation of the culture medium then begins.

According to FIG. 7d, at the time T1 after an incubation time, the presence of a first zone of inhibition 9 of the sample 1 is determined, for example by visual analysis. Indeed, some droplets exhibit bacterial growth 1a, while others do not exhibit any bacterial growth, 1c. At the intersection between the first zone of inhibition 9 and the zone of deposition 8 of the sample, certain droplets exhibit a growing portion and an inhibited portion 1b. It is thus possible at this time to demonstrate the presence of microorganisms in the sample and also the inhibition of the growth of these microorganisms in the presence of the chemical agent 5.

According to FIG. 7e, at the time T2 after a longer incubation time, the surface of the first zone of inhibition 9 is stable and no longer varies. It is thus possible at this time to reliably measure the size of the zone of inhibition and to deduce therefrom the value F corresponding to the minimum inhibitory concentration of the chemical agent. This value F corresponds to the concentration of chemical agent soaked on the strip at the intersection between the zone of growth and the zone of inhibition of the sample.

In the case in which the medium only exhibits droplets with bacterial growth 1a or without bacterial growth 1c, the value F corresponds to the intermediate value obtained by plotting a line perpendicular to the axis 7 between the last inhibited droplet and the first growing droplet in the direction of increasing concentrations of the strip, and by observing the corresponding value of the concentration of chemical agent on the strip.

In the case in which the medium exhibits a droplet with a growing portion and an inhibited portion 1b, the value F may especially be obtained by seeking an arc or a straight line at the boundary between the growing portion and the inhibited portion; by seeking the intersection of this arc or this straight line with the long edge 3a of the strip and by observing the value of the concentration of chemical agent at this intersection. Alternatively, the droplets exhibiting a growing portion and an inhibited portion 1b may be ignored in order to seek the first higher value of concentration which is completely inhibiting the growth of a droplet.

Figure 7F:
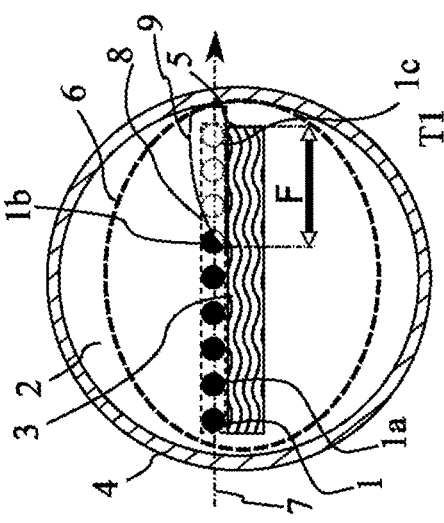

According to FIG. 7f, it is possible that, at a time T2, the first zone of inhibition 9 is no longer visible or is greatly reduced and that some, or even all, of the droplets exhibit bacterial growth 1a. It is thus possible at this time to determine that the microorganism present in the sample 2 is resistant to the chemical agent 5. It is also possible that no zone of inhibition is apparent, regardless of the duration of incubation, demonstrating the resistance of the microorganism to the chemical agent.

Figure 8D:
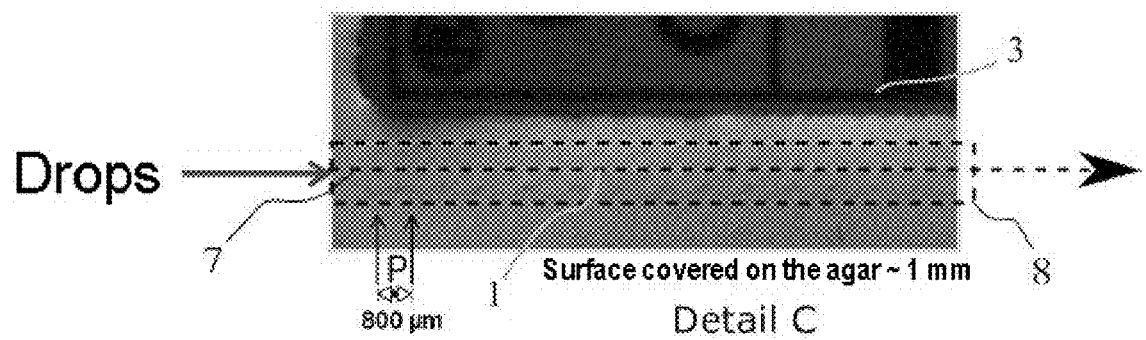

FIGS. 8a to 8d and 9a to 9d illustrate this second example of implementation of the invention. According to FIG. 8a, a sample 1 is deposited in the form of a series of droplets, along an axis parallel to the long edge of a strip 3 containing a concentration gradient of chemical agent. The strip 3 comprises graduations of concentrations of chemical agent 13, making it possible to deduce a minimum inhibitory concentration of chemical agent. An example of such a strip is sold by the applicant under the trade name Etest®. According to the FIG. 8b, a strip 3 containing a chemical agent 5 is deposited on a culture medium 2 contained in a Petri dish 4 (for example a Petri dish with a diameter greater than or equal to 9 cm). The detail B in FIG. 8b is visible in FIG. 8c. A sample 1 is deposited in the form of a series of droplets in a deposition zone 8 along an axis 7 parallel to the long edge of the strip 3. In this example, 13 nanoliter drops are deposited by a Pipejet P9 Nanodispenser pipette sold by the company biofluidix and mounted on a robotic arm. The detail C in FIG. 8c is visible in FIG. 8d. 50 droplets are thus deposited along the axis 7 with an interval P of 800 µm. Each droplet covers a surface area of approximately 1 mm².

According to a first experiment of this example, an inoculum of a strain of *Escherichia coli* ATCC 35218 (American Type Culture Collection) having a concentration of 0.5 McFarland is thus deposited in droplets along four Etest® strips (bioMérieux), each deposited on a Mueller Hinton E agar culture medium (bioMérieux). The strips contain respectively a concentration gradient of gentamicin, tetracycline, ampicillin/sulbactam, ampicillin. In the same manner, an inoculum of a strain of *Escherichia coli* ATCC 25922 having a concentration of 0.5 McFarland is deposited in droplets along four Etest® strips (bioMérieux), each deposited on a Mueller Hinton E agar culture medium (bioMérieux). The strips also contain a concentration gradient of gentamicin, tetracycline, ampicillin/sulbactam, ampicillin.

Fifty droplets, each with a volume of 13 nanoliters and spaced apart by 800 µm, are deposited along each strip. As a function of the concentration of 0.5 McFarland, it is thus estimated that approximately 2000 bacteria are present in each droplet. The eight culture media prepared in this way are then incubated and monitored periodically in order to determine the presence or the absence of a zone of inhibition and/or of growth of the microorganisms.

FIGS. 9a to 9d illustrate a plan view of the four media in which the sample of *Escherichia coli* ATCC 35218 was deposited. FIGS. 9a to 9d are obtained by means of a shadowgraphy capture device as presented in relation to FIG. 5. FIG. 9a presents a view after 5 hours of incubation of the sample in the presence of gentamicin. The sample then exhibits growing droplets 1a, droplets in which growth is inhibited 1c, and at least one partially inhibited droplet 1b. Using conventional techniques for analysis of the image of the partially inhibited droplet 1b, a straight line 14 is obtained, perpendicular to the long edge of the strip and delimiting the boundary of the zone of growth of the microorganisms and the zone of inhibition. A minimum inhibitory concentration value is then obtained at the intersection between the straight line 14 and the long edge of the strip. A minimum inhibitory concentration (MIC) of 2 µg/ml is thus determined.

Advantageously, a straight line or an arc 15 delimiting the boundary of the zone of growth of microorganisms and the zone of inhibition may be sought, this straight line not necessarily being perpendicular to the long edge and thus reproducing said boundary more faithfully. This straight line or this arc corresponds to a portion of the ovoid area of inhibition observed with conventional inoculation methods and therefore enables better estimation of the MIC. In the case in which a straight line or an arc 15 is sought, the minimum inhibitory concentration may be obtained by tracing a line perpendicular to the long edge of the strip, crossing the point of intersection between the straight line 15 and the axis of deposition of the sample 7, then by seeking the graduation corresponding to this perpendicular line on the strip.

FIG. 9b presents a view after 5 hours of incubation of the sample in the presence of tetracycline. A similar method is repeated and makes it possible to estimate a minimum inhibitory concentration of 1.5 µg/ml. FIG. 9c presents a view after 5 hours of incubation of the sample in the presence of ampicillin/sulbactam. A similar method is repeated and makes it possible to estimate a minimum inhibitory concentration of 18 µg/ml. FIG. 9d presents a view after 5 hours of incubation of the sample in the presence of ampicillin. In this figure, only growing droplets 1a are observed, demonstrating the resistance of the microorganism to ampicillin; the observed value of minimum inhibitory concentration is thus greater than 256 µg/ml.

The minimum inhibitory concentration results obtained for the strains of *Escherichia coli* ATCC 35218 and also the strains of *Escherichia coli* ATCC 25922 are compared with the conventional method by flooding of the medium in table 1 below. The values are given in µg/ml at different incubation times. The inhibition values for the flooding method are measured from images obtained by a shadowgraphy capture device as described above. The inhibition values for the method according to the invention are measured from images obtained by a shadowgraphy capture device at 5 hours, and visually at 7 hours.

TABLE 1

| Strain | | | | ATCC 35218 | | | | |
|---|---|---|---|---|---|---|---|---|
| Gentamicin | Incubation time | 4 H | 5 H | 6 H | 7 H | 8 H | 24 H | |
| | Flooding | 0.96 | 1.14 | 1.17 | | 1.17 | 1.06 | |
| | Deposition in droplets | | 2 | | 2 | | | |
| Tetracycline | Incubation time | 4 H | 5 H | 6 H | 7 H | 8 H | 24 H | |
| | Flooding | 0.44 | 0.86 | 0.96 | | 1.117 | 2.3 | |
| | Deposition in droplets | | 1.5 | | 2 | | | |
| Ampicillin/Sulbactam | Incubation time | | 5 H | 6 H | 7 H | 8 H | 20 H | |
| | Flooding | | | 10.85 | | 12.29 | 12.3 | |
| | Deposition in droplets | | 18 | | 18 | | | |
| Ampicillin | Incubation time | | 5 H | 6 H | 7 H | 8 H | 18 H | |
| | Flooding | | | R | | R | R | |
| | Deposition in droplets | | R | | R | | | |
| Strain | | | | ATCC 25922 | | | | |
| Gentamicin | Incubation time | 4 H | 5 H | 6 H | 7 H | 8 H | 24 H | |
| | Flooding | 1.74 | 1.51 | 1.75 | | 1.82 | 1.54 | |
| | Deposition in droplets | | 2 | | 2 | | | |
| Tetracycline | Incubation time | 4 H | 5 H | 6 H | 7 H | 8 H | 24 H | |
| | Flooding | 0.3 | 0.6 | 0.66 | | 0.86 | 1.77 | |
| | Deposition in droplets | | 1.5 | | 2 | | | |
| Ampicillin/Sulbactam | Incubation time | | 5 H | | 7 H | | | |
| | Flooding | | | | | | | |
| | Deposition in droplets | | 4 | | 6 | | | |
| Ampicillin | Incubation time | | 5 H | 6 H | 7 H | 8 H | 18 H | |
| | Flooding | | | 3.43 | | 5.21 | 5.69 | |
| | Deposition in droplets | | 8 | | 8 | | | |

R = resistant, values in µg/ml

Table 1 makes it possible to conclude that there is a good correlation of the MICs estimated between the conventional method and the method according to the invention. It is noted that small differences in the values obtained may be observed in the case in which the deposition of the droplets is too far away from the long edge of the strip, or is not carried out parallel to the long edge. An optimal position of the axis of deposition of the sample, 1 mm away from the strip and parallel to the long edge, thus makes it possible to limit the differences in estimated MIC values. Moreover, it is clearly established that the dispensing of the sample by the PipeJet™ P9 Nanodispenser automated pipette (bioFluidix) does not prevent the growth of the bacteria tested. This experiment also demonstrates that it is possible to estimate an MIC with a sample of reduced volume, the total number of microorganisms deposited per culture medium being here estimated at 100 000 bacteria for the method according to the invention. Finally, a very high optical contrast is observed for shadowgraphy at 5 hours and visual analysis at 7 hours, making it possible to accelerate the method for determining the minimum inhibitory concentration by virtue of the deposition of the sample in droplets. This very high contrast also makes it possible to envisage the use of conventional image analysis techniques in order to determine this concentration value in an automated manner.

A second experiment of this example is conducted in order to evaluate the performance of the method according to the invention with samples with very low concentrations. For this purpose, three suspensions of Escherichia coli ATCC 35218, respectively at 0.5 McFarland, 0.1 McFarland and 0.01 McFarland are prepared. The MIC values are evaluated for each of these strains in the presence of a strip of gentamicin, of tetracycline, of ampicillin/sulbactam or of ampicillin. For this purpose, fifty droplets, each of 18 nanoliters, are deposited along an axis parallel to the long edge of each strip in a similar manner to the first experiment, for each of the concentration values. FIG. 10a illustrates a portion of the strip and the droplets close to said strip after 5 hours of incubation of the sample of Escherichia coli ATCC 35218 at 0.5 McFarland in the presence of ampicillin/sulbactam. FIG. 10b illustrates a portion of the strip and the droplets close to said strip after 5 hours of incubation of the sample of Escherichia coli ATCC 35218 at 0.01 McFarland in the presence of ampicillin/sulbactam. FIGS. 10a and 10b are obtained by a shadowgraphy capture device as presented above. These two figures make it possible to determine the presence of a zone of inhibition and to estimate an MIC at 10 µg/ml, even at a very low concentration. The following table 2 presents the results of this second experiment in comparison with a conventional flooding method.

TABLE 2

| | | ATCC 35218 | | | | | | |
|---|---|---|---|---|---|---|---|---|
| Strain | | 4 H | 5 H | 8 H | 7 H | 8 H | 18 H | 28 H |
| Gentamicin | flooding | 0.96 | 1.14 | 1.17 | | 1.17 | | 1.06 |
| 0.5 McF | droplet/replicate 1 | | 2 | | 2 | | | |
| 0.5 McF | droplet/replicate 2 | 2 | | 1.5 | | | | |
| 0.1 McF | droplet | 2 | | 2 | | | | |
| 0.01 McF | droplet | 1.3 | 1.3 | | | | | |
| Tetracycline | flooding | 0.44 | 0.86 | 0.96 | | 1.117 | | 2.3 |
| 0.5 McF | droplet | | 1.5 | | 2 | | | |
| Ampicilline | flooding | | | R | | R | | R |
| 0.5 McF | droplet | | R | | R | | | |

TABLE 2-continued

| | | ATCC 35218 | | | | | | |
|---|---|---|---|---|---|---|---|---|
| Strain | | 4 H | 5 H | 8 H | 7 H | 8 H | 18 H | 28 H |
| Ampicillin Sulbactam | flooding | | | 10.85 | | 12.29 | | 12.3 |
| 0.5 McF | droplet/replicate 1 | | <16 | | <16 | | | |
| 0.5 McF | droplet/replicate 2 | 10 | | 10 | | | | |
| 0.1 McF | droplet | 10 | | 10 | | | | |
| 0.01 MCF | droplet | 10 | 10 | | | | | |

R = resistant, values in µg/ml

This second experiment also makes it possible to conclude that there is a good correlation between the MICs determined by the droplet method according to the invention and the flooding method. This experiment also demonstrates that the method according to the invention makes it possible to estimate an MIC with a sample of reduced volume and at low concentration, the total number of microorganisms deposited being here estimated at 2000 bacteria, i.e. 50 drops containing 40 bacteria on average. Finally, a very high optical contrast is also observed for shadowgraphy at 5 hours and visual analysis at 7 hours, making it possible to accelerate the method for determining the minimum inhibitory concentration.

A third method of implementation of the invention is illustrated by FIGS. 11a, 11b and 12. In this method, the sample is deposited by smearing on the surface of the culture medium (e.g. agar in a Petri dish with a diameter greater than or equal to 9 cm) by means of a sampling tool such as described in the international application published under the number WO2012/083150. Such an integrated device makes it possible to carry out one or more filtration steps and also to transfer a liquid sample. Said device comprises a tubular portion, one of the ends of which is covered with a filtration material such as a membrane, said filtration material being arranged outside this end and covering it totally. The other end of the tubular portion is able to be connected to a suction or dispensing means such as a vacuum pump. The benefit of using such a tool especially being able to estimate the MIC of a sample originating from a positive blood culture bottle, that is to say one which has a result confirming the presence of microorganisms after a given incubation time. For this purpose, the sample may especially be prepared by taking off a volume of the positive blood culture, carrying out a step of lysis, for example chemical lysis, of the blood cells of the volume taken off, then by carrying out filtration of the lysed volume by suction at the surface of a membrane. The microorganism concentrate may then be deposited directly on a culture medium by affixing the membrane covering the end of the sampling tool to the surface of the agar culture medium, then in moving it over the surface of the culture medium 2 along an axis 7 as illustrated in FIG. 11a. The operation may be carried out again in order to deposit the sample along a second axis 7'. A strip 3 containing a chemical agent is deposited parallel to the axis 7 and advantageously between the two axes 7 and 7'. The surface covered by the zone(s) of deposition 8, 8' must then preferentially be adjacent to the edge of the strip so as not to be directly in contact with same, and to avoid the effects of diffusion of chemical agent.

An example of this third method of implementation of the invention will now be described. An Etest® strip 3 of gentamicin (bioMérieux) is deposited on a Mueller Hinton E agar 2 (bioMérieux, Ref. 413822). A suspension of *Escherichia coli* ATCC 25922 calibrated to 0.5 McFarland is prepared.

In order to carry out this operation in an automated manner, the support of the agar is placed on a motorized platform moving translationally along an axis X, the axis of the strip being parallel to this axis. The sampling tool is supported by a motorized arm moving translationally along a substantially vertical axis Z. With reference to the FIG. 13, the sampling tool 30 comprises a tubular body 32 comprising one end covered with a PES Supor® membrane 34 with a 0.45 µm porosity (Pall). The other end 42 is open, so as to be able to be connected to a suction means such as a vacuum pump. In the body 32, and between the membrane 34 and the end 42, the following are arranged: a fibrous portion 36 such as cotton, a set of glass beads 38, the diameter of which is between 212 µm and 300 µm, the beads being held by a fibrous portion 40 made of cotton. The benefit of these different portions is described in more detail in the international patent published under the number WO2012/083150. The following protocol is carried out in order to prepare the sample:

1 ml of a positive blood culture bottle is taken off then mixed by three cycles of aspiration/dispensation with 0.5 ml of lysis buffer (0.45% w/v Brij-97+0.3 M CAPS, pH 11.7) by means of a pipette in a container.
  The mixture is incubated for two minutes at room temperature in order to obtain a lysed sample.
  Following the incubation, the end supporting the membrane 34 of the sampling tool 30 is submerged in the lysed sample then filtered by suction at −600 mbar for 2 minutes.
  The sampling tool is then moved to another container comprising a first washing solution (Brij/Saline solution (0.45% w/v NaCl+0.05% Brij 97)).
  The end supporting the membrane 34 of the sampling tool 30 is submerged in the first washing solution then suctioned (at −600 mbar) for 4 minutes.
  The sampling tool is then moved to another container comprising a second washing solution (deionized water).
  The end supporting the membrane 34 of the sampling tool 30 is submerged in the second washing solution then suctioned (at −600 mbar) for 3 minutes then 20 seconds of suction outside the container in order to limit the appearance of bubbles in the sampling tool 30.
  The microorganisms contained in the sample are thus concentrated at the surface of the membrane 34.

In accordance with the FIG. 11a, the sample 1 prepared in this way by filtration is then deposited by moving the membrane 34 in a Z of 150 µm from the surface of the agar in order to very gently introduce it into the agar. The membrane is then moved along the axis X for 65 mm at constant Z. In order to be able to precisely measure the Z movement of the sampling tool, conventional techniques for detecting the surface of the agar may be used.

The sample is thus deposited along two axes, 7, 7', adjacent and parallel to the long edges of the Etest® strip 3 of gentamicin. Thus, the two zones of deposition 8, 8' obtained have uniform distribution which is adjacent to the long edges of the strip.

Each zone of deposition has a width of approximately 2 mm. The culture medium inoculated in this way is incubated at 35° C. Plan-view images of the medium are captured by means of a shadowgraphy capture device at regular time intervals. Visual examination is also carried out. FIG. 11a presents an image captured by shadowgraphy after 3 h 30 of incubation. FIG. 11b presents an image captured by shadowgraphy after 6 h 30 of incubation. FIG. 12 is a photograph of the same dish in natural light after 6 h 30 of incubation.

It is thus possible, from 3 h 30 of incubation, to detect the presence of a zone of inhibition of the sample 1c and of a zone of growth of the microorganisms present in the sample 1a. It is also possible to determine a minimum inhibitory concentration of 1.5 µg/ml from images obtained by shadowgraphy. A visual examination at 6 h 30 also confirms this value, as illustrated in FIG. 12. The benefit of this method is therefore to be able to determine an MIC from a very small volume of sample and with a restricted number of handling operations which can readily be automated. The deposition movement at the surface of the agar may also be performed by a robotic arm or a tool holder moving translationally along three axes of freedom.

The methods and devices described in the present invention may be implemented by one or more computer programs, which may be present in various active and inactive forms, on a single computer or spread over computer systems. For example, they may be implemented by software comprising instructions able to implement the methods of the present invention and described in the form of source code, object code, executable code or any format enabling certain steps of the methods according to the invention to be carried out, especially the steps consisting in:

Determining the presence or the absence of said first zone of inhibition.

Determining the number of inhibited droplets in the potential zone of inhibition and/or the number of non-inhibited droplets in the zone of deposition of the sample.

Measuring the distance between the center of the disk and the first zone of inhibition so as to estimate the sensitivity of the microorganisms contained in the sample to the chemical agent.

Classifying the microorganism according to a classification containing three criteria: Sensitive, Intermediate or Resistant, from a sensitivity chart corresponding to the microorganism present in the sample and to the chemical agent, this chart being for example available on a storage device.

Locating a boundary between the first zone of inhibition and the zone of growth of the microorganisms.

Determining a minimum inhibitory concentration of the chemical agent from the location of said boundary.

All these computer programs may be stored on a readable storage device for computer, which includes storage devices and corresponding signals, in compressed or decompressed form.

The term computer refers to any electronic device comprising a processor, such as a central processing unit (CPU), a dedicated processor or a microcontroller. A computer is capable of receiving data (one or more inputs), of carrying out a sequence of predetermined steps on this data, and of producing a result in the form of information or signals (one or more outputs). Depending on the context, the term computer may mean a processor in particular or more generally a processor combined with a set of interconnected elements contained in a single casing.

The term readable storage device for computer or storage device refers to any means for containing, storing, communicating, distributing or transporting the computer program for the use thereof by, or in relation with, a computer or any other means for executing said program. The readable storage device for computer may be, nonlimitingly, an electronic, magnetic, optical, electromagnetic or infrared system or a system containing semiconductors, and also an apparatus, device or means for propagating said program. More specific nonlimiting examples of storage devices may be a diskette, a CD-ROM, random-access memory (RAM), read-only memory (ROM), erasable programmable read-only memory (EPROM or FLASH storage), an optical fiber or else any electrical connection comprising one or more cables.

The invention also relates to a system comprising a computer and also to one or more computer programs configured to implement one or more methods according to the invention. Advantageously, said system also comprises means for controlling a capture device able to capture images of the culture medium after incubation, the captured images being processed by said computer program. Advantageously, said system also comprises means for moving the culture medium, such as motorized platforms and means for controlling these movement means. Advantageously, said system also comprises automated means for depositing the sample, such as robotic arms, pipetting robot, etc., and also means for controlling these deposition means.

The invention claimed is:

1. A method for detecting a presence or an absence of at least one zone of inhibition, the method comprising:

providing a support impregnated with a determined amount of a chemical agent on a surface of an agar culture medium before or after sample deposition such that the chemical agent defines a potential inhibition zone;

depositing a volume of a sample in liquid form that contains or is liable to contain microorganisms on the surface of the agar culture medium within a deposition zone extending along an axis at the surface of the agar culture medium so that only a portion of the surface of the agar culture medium is covered with the volume of the sample;

incubating the agar culture medium with the chemical agent and the volume of the sample on the surface of the agar culture medium; and determining the presence or absence of the zone of inhibition after incubation, wherein:

the deposition zone intersects the potential inhibition zone; and the volume of the sample is deposited in a series of droplets in which each droplet of the series of droplets is from the same sample.

2. The method of claim 1, further comprising obtaining the sample by pre-culturing a crude sample that includes isolating a microorganism strain and incubating the microorganism strain for less than 10 hours so as to increase microorganism biomass.

3. The method of claim 2, wherein the sample contains a known type of microorganism prior to the volume of the sample being deposited on the surface of the agar culture medium.

4. The method of claim 1, wherein the droplets are spaced apart by a predetermined interval.

5. The method of claim 1, wherein the droplets are spaced apart by an interval in a millimeter range.

6. The method of claim 1, wherein each droplet has a volume between 1 nl and 10 µl.

7. The method of claim 1, wherein an amount of microorganisms contained in each droplet is known and is between 1 microorganism per droplet and $10^6$ microorganisms per droplet.

8. The method of claim 1, further comprising determining number of inhibited droplets and/or non-inhibited droplets.

9. The method of claim 1, wherein the support is a disk that contains the determined amount of the chemical agent.

10. The method of claim 9, further comprising measuring a distance between center of the disk and the zone of inhibition so as to estimate a sensitivity of the microorganisms contained in the sample to the chemical agent.

11. The method of claim 10, further comprising classifying the microorganisms as Sensitive, Intermediate or Resistant to the chemical agent.

12. The method of claim 1, wherein the support is a strip containing a concentration gradient of the chemical agent and the volume of the sample is deposited parallel and adjacent to a long edge of the strip.

13. The method of claim 12, further comprising:
locating a boundary between the zone of inhibition and a zone of growth of the microorganisms; and
determining a minimum inhibitory concentration of the chemical agent from location of the boundary.

14. The method of claim 1, wherein deposition of the volume of the sample is automated.

15. The method of claim 1, wherein the volume of the sample is deposited so as to be spaced from a periphery of the agar culture medium.

16. The method of claim 1, wherein the volume of the sample is deposited so as to not contact sides of a Petri dish containing the agar culture medium.

17. A method for detecting a presence or an absence of at least one zone of inhibition, the method comprising:
obtaining a sample by pre-culturing a crude sample that includes isolating a microorganism strain and incubating the microorganism strain for less than 10 hours so as to increase microorganism biomass;
providing a determined amount of a chemical agent on a surface of an agar culture medium before or after sample deposition such that the chemical agent defines a potential inhibition zone;
depositing a volume of the sample in liquid form on the surface of the agar culture medium within a deposition zone extending along an axis at the surface of the agar culture medium so that only a portion of the surface of the agar culture medium is covered with the volume of the sample;
incubating the agar culture medium with the chemical agent and the volume of the sample on the surface of the agar culture medium; and
determining the presence or absence of the zone of inhibition after incubation, wherein:
the deposition zone intersects the potential inhibition zone; and
the volume of the sample is deposited in a continuous line.

18. The method of claim 17, wherein the sample contains a known type of microorganism prior to the volume of the sample being deposited on the surface of the agar culture medium.

19. The method of claim 17, wherein the sample has a concentration of between 0.0005 McFarland and 0.5 McFarland.

20. The method of claim 17, wherein a support impregnated with the determined amount of the chemical agent is provided on the surface of the agar culture medium.

21. The method of claim 20, wherein the support is a disk that contains the determined amount of the chemical agent.

22. The method of claim 21, further comprising measuring a distance between center of the disk and the zone of inhibition so as to estimate a sensitivity of the microorganisms contained in the sample to the chemical agent.

23. The method of claim 22, further comprising classifying the microorganisms as Sensitive, Intermediate or Resistant to the chemical agent.

24. The method of claim 20, wherein the support is a strip containing a concentration gradient of the chemical agent and the volume of the sample is deposited parallel and adjacent to a long edge of the strip.

25. The method of claim 24, further comprising:
locating a boundary between the zone of inhibition and a zone of growth of the microorganisms; and
determining a minimum inhibitory concentration of the chemical agent from location of the boundary.

26. The method of claim 17, wherein deposition of the volume of the sample is automated.

27. The method of claim 17, wherein the volume of the sample is deposited so as to be spaced from a periphery of the agar culture medium.

28. The method of claim 17, wherein the volume of the sample is deposited so as to not contact sides of a Petri dish containing the agar culture medium.

* * * * *